United States Patent [19]

Geddes et al.

[11] Patent Number: 4,606,352

[45] Date of Patent: Aug. 19, 1986

[54] PERSONAL ELECTROCARDIOGRAM MONITOR

[75] Inventors: Leslie A. Geddes; Neal E. Fearnot, both of West Lafayette, Ind.

[73] Assignee: Purdue Research Foundation, West Lafayette, Ind.

[21] Appl. No.: 630,589

[22] Filed: Jul. 13, 1984

[51] Int. Cl.[4] .............................................. A61B 5/04
[52] U.S. Cl. .................................... 128/702; 128/712
[58] Field of Search .............. 128/696, 710, 701, 702, 128/712, 703, 700, 708

[56] References Cited

U.S. PATENT DOCUMENTS

| | | |
|---|---|---|
| 3,732,868 | 5/1973 | Willems et al. . |
| 3,792,700 | 2/1974 | Sarnoff et al. . |
| 3,809,071 | 5/1974 | Davolos et al. ..................... 128/702 |
| 3,848,582 | 11/1974 | Milani et al. . |
| 3,858,576 | 1/1975 | Dehnert et al. ..................... 128/712 |
| 4,230,127 | 10/1980 | Larson . |
| 4,250,503 | 2/1981 | Shanks . |
| 4,250,888 | 2/1981 | Grosskopf ........................... 128/702 |
| 4,346,378 | 8/1982 | Shanks . |
| 4,350,164 | 9/1982 | Allain, Jr. . |

FOREIGN PATENT DOCUMENTS 82736 1/1982 Japan .
1597355 9/1981 United Kingdom .

OTHER PUBLICATIONS

Adler et al, "Medical Instrumentation", vol. 13, No. 4, Jul.-Aug. 1979, pp. 216-217.
"Hand-Size, But Here At Last: Flat-Screen Color TV", Popular Science, Nov. 83, vol. 223, pp. 100-102.

Primary Examiner—William E. Kamm
Attorney, Agent, or Firm—Woodard, Weikart, Emhardt & Naughton

[57] ABSTRACT

A pocket-sized, self-contained electrocardiogram monitor with a dot-matrix, liquid-crystal display. The monitor uses dry electrodes and is suitable for direct placement against the patient's chest without the use of paste or gel to insure electrical contact. An A/D converter converts an ECG signal to a digital signal which is then processed by a microprocessor and then displayed on the liquid-crystal display in real time. The microprocessor is programmed to select the maximum and minimum digital values from four consecutive samples from the A/D converter and to supply data representative of the maximum and minimum values to the display at one-fourth the conversion sampling rate.

7 Claims, 5 Drawing Figures

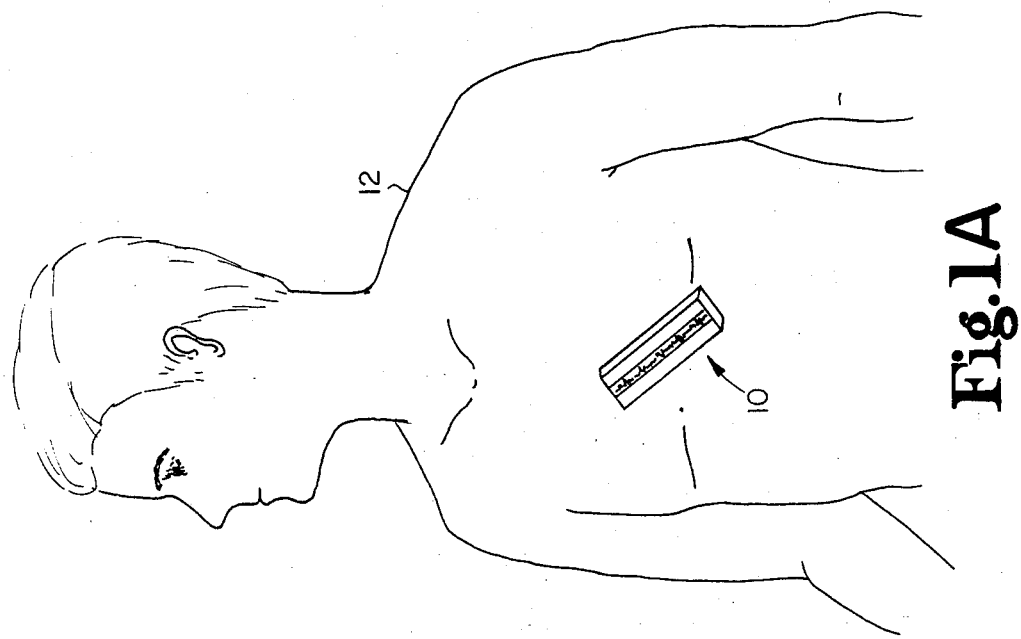
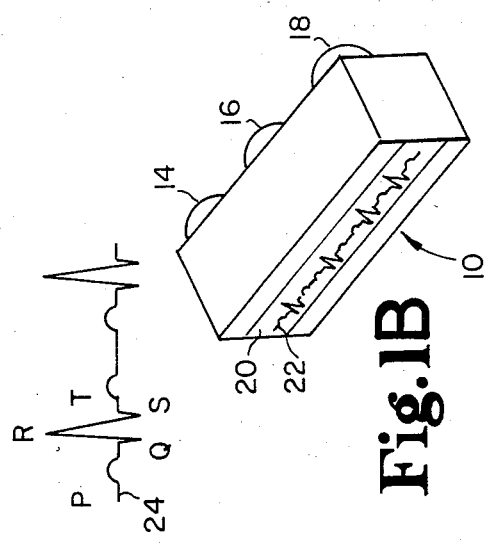
Fig.1A
Fig.1B
Fig.1C

PERSONAL ELECTROCARDIOGRAM MONITOR

STATEMENT OF GOVERNMENT RIGHTS

This invention was made with Government support under Grant No. 1 RO3 RR02144 awarded by the National Institutes of Health. The Government has certain rights in the invention.

BACKGROUND OF THE INVENTION

This invention relates to equipment for monitoring the electrical activity of the heart in a living body, and particularly to portable electrocardiograph monitors.

A number of portable devices exist for monitoring the electrical activity of the heart. U.S. Pat. No. 4,351,164 to Allain, Jr. discloses a self-powered life monitor in a pocket-sized, tubular container with electrode probes on one end which are capable of piercing the skin to rest in subcutaneous tissue and an LED light source on the other end to indicate the existence and strength of an electrical potential indicative of bioelectric activity.

Sarnoff et al., in U.S. Pat. No. 3,792,700, describes a handheld battery-operated cardiac monitor which converts a signal picked up by two spaced electrodes on the body to pulsing light or to an audible beeping signal indicative of the heart beat. The monitor is provided with a flashing lamp and audible monitor and is attached via two electrical leads to two electrodes placed in the user's armpits.

ECG telephone transmitters using armpit electrodes of the type shown in Sarnoff et al. are also known. The ECG signal is tone-frequency modulated for transmission along telephone lines.

U.S. Pat. No. 3,732,868 to Willems, et al. shows a device for the audible reproduction of an electrocardiogram signal with speech-like sounds. Three electrodes arranged in a triangular pattern are attached to the device housing by means of three L-shaped contact arms.

A number of cardiac monitoring devices are capable of being worn on the wrist of a user. One example of such a device is shown in U.S. Pat. No. 4,230,127 to Larson. This apparatus displays a count in beats per minute. The circuitry includes means for automatically turning the system off when no heartbeats are detected for a six-second interval.

During emergency medical diagnosis, an immediate record of the electrocardiogram (ECG) is highly desired to indicate if the victim has a major cardiac arrthymia such as tachycardia, fibrillation or asystole. Palpation of the pulse only indicates if the heart is or is not ejecting blood. The stethoscope can identify that the heart is or is not beating, but it cannot identify the nature of abnormal cardiac excitation and recovery. Only the ECG can provide this information. At present, no personal, pocket-sized ECG monitor for such a purpose exists.

Portable ECG monitors are also available with cathode-ray tube (CRT) display of the ECG. U.S. Pat. No. 3,848,582 to Milani et al. describes a CRT unit consisting of a battery-powered cathode ray oscilloscope in a metallic housing with pickup electrodes provided directly on the back of the housing and a pistol grip underneath the housing. It is not necessary to use electrode gel with this apparatus to insure proper contact with the patient's skin. The CRT display surface is on the order of 2 inches by 3 inches, and the total depth of the apparatus is approximately 6 to 8 inches. Although a CRT unit is relatively small and lightweight in comparison with the expensive and cumbersome devices used for ECG monitoring in hospitals, it is quite bulky and heavy compared to other portable cardiac monitors. Also, the high power consumption of the CRT causes excessively rapid battery drain which could lead to complete loss of power in a critical situation. This fact severely undermines the confidence which an emergency medical technician might have in using such an apparatus.

Shanks, in U.S. Pat. Nos. 4,250,503 and 4,346,378, describes a dot-matrix, liquid-crystal display (LCD) for display of sine waves and other continuous waveforms. A waveform to be displayed is periodically sampled using an A/D converter, and binary numbers representative of the amplitude of each sample are stored, either in a serial shift register or in a random-access memory (RAM). The stored information is then displayed at an appropriate rate for the LCD.

Liquid crystals with response time of less than 50 milliseconds are currently used in a miniature television manufactured by Seiko, according to an article entitled "Flat-screen color TV," by Herbert Shuldiner, published in the November, 1983 issue of Popular Science.

SUMMARY OF THE INVENTION

The present invention overcomes these and other disadvantages of the prior art by providing a handheld, self-contained electrocardiogram monitor comprising a housing with a plurality of electrodes mounted thereon for contact with the patient's chest, circuit means contained within the housing for processing an electrocardiographic signal appearing on the electrodes when the housing is held against the patient's chest with the electrodes in contact therewith, and a liquid-crystal display (LCD).

According to a further aspect of the invention, a portable electrocardiogram monitor is provided which is pocket-sized, operates with dry electrodes, and includes circuit means for processing the electrocardiographic signals and displaying it on an LCD.

A general object of the invention is to provide an improved portable electrocardiogram monitor.

Another object of the invention is to provide a pocket-sized, completely self-contained electrocardiogram monitor.

Another object of the invention is to provide a completely self-contained electrocardiogram monitor with long battery life.

Another object is to provide a personal electrocardiogram monitor which is easy to handle and simple to use.

BRIEF DESCRIPTION OF THE DRAWINGS

FIG. 1A is a perspective view of the preferred embodiment of the ECG monitor according to the present invention, particularly illustrating the application of the monitor to a patient's chest.

FIG. 1B is a magnified, perspective view of the ECG monitor shown in FIG. 1A.

FIG. 1C illustrates a portion of the signal tracing shown in FIGS. 1A and 1B.

DESCRIPTION OF THE PREFERRED EMBODIMENT

Figure 2:
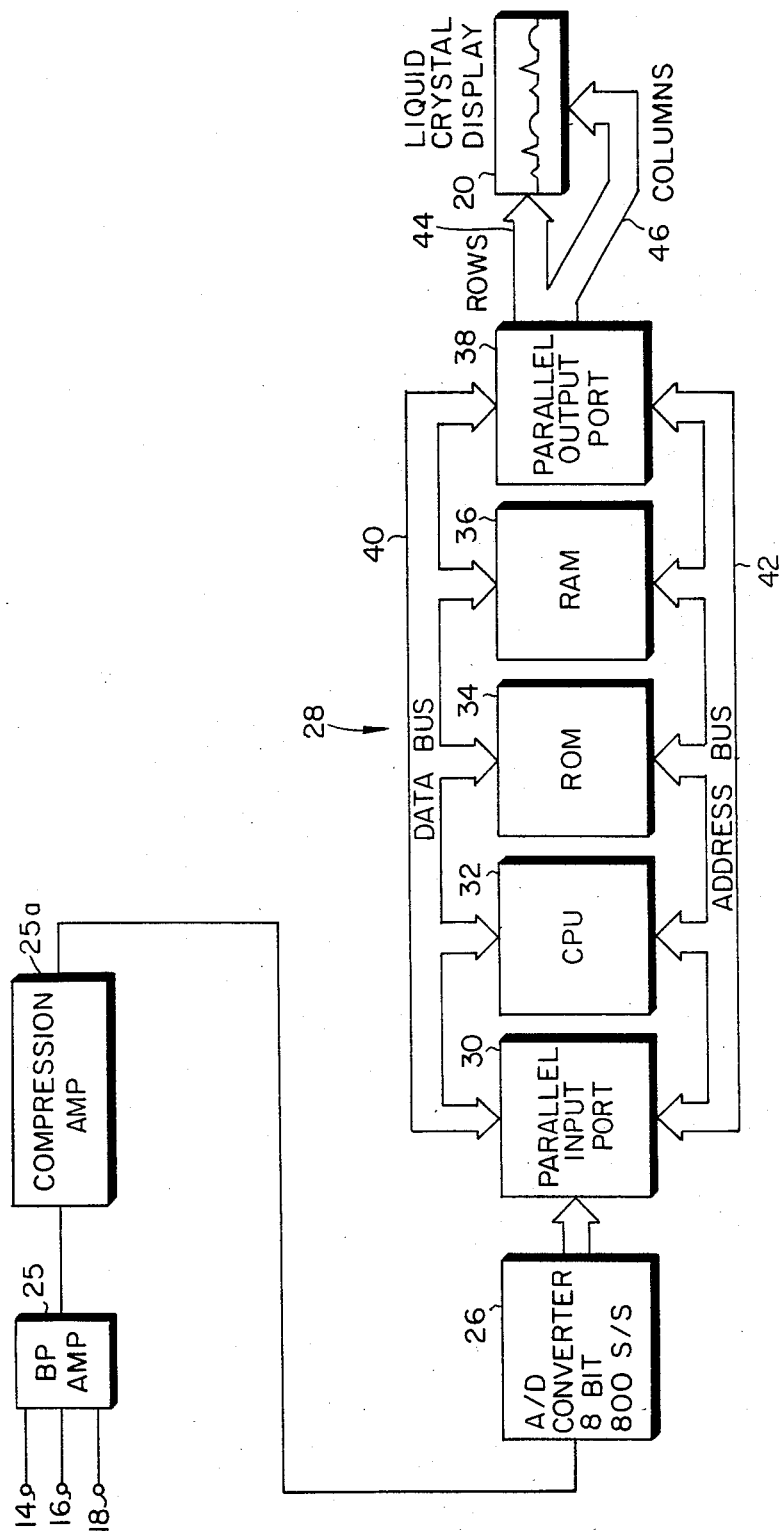
FIG. 2 is a block diagram representation of the internal circuitry of the ECG monitor shown in FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

With reference to FIG. 1, a personal ECG monitor 10 according to the present invention is shown in operating position in contact with the chest of a patient 12 and is additionally shown in a magnified view illustrating the three electrodes 14, 16, and 18 on the back of the unit. The front side of monitor 10 includes a liquid-crystal display (LCD) 20, adapted to provide an ECG signal tracing 22 with its time axis parallel to the longitudinal axis of the monitor 10. A portion of signal tracing 22 is illustrated at reference numeral 24, which indicates the relative positions and amplitudes of the P, Q, R, S and T waves of a normal ECG signal.

Electrodes 14, 16, and 18 are dry electrodes mounted directly to the back side of monitor 10 in a longitudinal line. The use of dry electrodes eliminates the discomfort associated with pastes and gels used to make electrical contact between the patient's skin and the electrodes of conventional systems and additionally eliminates the time-consuming task of preparing the paste or gel and the skin. Electrodes of the type used for monitor 10 are preferably silver or silver chloride although conductive plastic and other metals are also suitable, and they exhibit typical impedance on the order of 100 to 1K ohms in the frequency range from 0.1 to 100 Hz. The electrodes further preferably have stability over time and repeated use, and minimal electrode polarization. Dry electrodes for use in ECG monitors are described by Geddes et al in *Ann. Biomed. Eng.* 1973, 1(3): 356–357.

The ECG signal appearing on the electrodes when monitor 10 is placed against the patient's skin is digitally processed before being supplied to LCD 20. Referring now to FIG. 2, the internal circuitry of ECG monitor 10 includes a bandpass amplifier 25 and an A/D converter 26 coupled to a microprocessor 28. A compression amplifier 25a is also optionally included between amplifier 25 and A/D converter 26 for enhancement of small signals near the baseline of the ECG signal, particularly for enhancement of the P-wave. In embodiments employing this amplifier, a 4:1 ratio from maximum to minimum gain is recommended.

Bandpass amplifier 25, connected to the electrodes 14, 16 and 18, is a high-gain differential amplifier which filters and amplifies the received ECG signals before conversion to digital form. Amplifier 25 has a pass band from 0.5 to 80 Hz. gain of approximately 2000, common-mode rejection ratio of at least 80 db and preferably 120 db, and 10-megohm input impedance. Input impedance of this magnitude is required because of the relatively high source impedance exhibited by dry electrodes. The filter parameters described above have been found to be most effective for filtering out unwanted noise components in the signal received from dry electrodes of the type described above. However, other suitable bandpass characteristics may be used.

The A/D converter 26 receives the ECG signal from bandpass amplifier 25 or, in the alternative embodiment described above, from compression amplifier 25a, and converts it to a digital signal with an amplitude resolution of 8 bits, or 256 levels, operating with a sampling rate of 800 samples per second. The digital signal output of A/D converter 26 thus contains 800 8-bit binary numbers each second. These binary values are supplied to parallel input port 30 of microprocessor 28, which also includes a central processing unit (CPU) 32, a ROM 34, a RAM 36 and a parallel output port 38, all interconnected by a data bus 40 and an address bus 42. Microprocessor 28 and A/D converter 26 are provided with a common clock signal for synchronization of the conversion and processing of the ECG signal to be displayed. This circuit is also provided with high-voltage protection and is capable of rapid recovery after a defibrillation shock is delivered.

Figure 3:
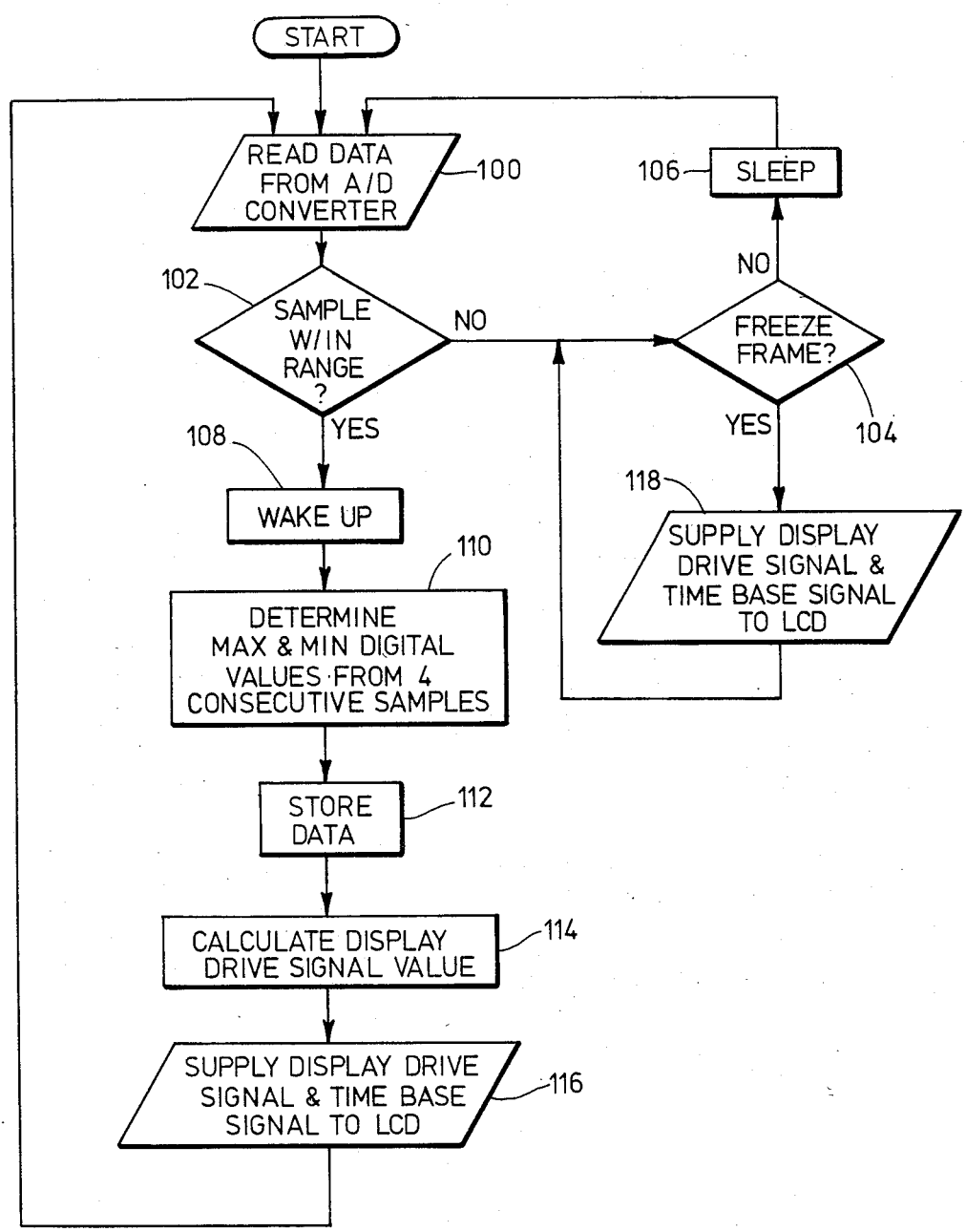
FIG. 3 is a flowchart illustrating the program executed by the microprocessor in the preferred embodiment of the ECG monitor according to the present invention.

A program stored in ROM 34 causes CPU 32 to process the incoming digital signal received from A/D converter 26 through parallel input port 30 and data bus 40 and to generate a time base signal. That program is illustrated by the flowchart of FIG. 3. CPU 32 applies the address for input port 30 to address bus 42 once for each sample of the ECG signal. The program stored in ROM includes an algorithm, illustrated by steps 110, 112, 114, and 116 of FIG. 3, whereby CPU 32 determines the maximum and minimum digital values from four consecutive samples and stores only those two values in RAM 36. In step 114, CPU 32 calculates a display drive signal value for a particular column of display 20 based on the selected maximum and minimum values and the display drive input format, and in step 116 supplies the drive signal on output lines 44 as a row-address signal to liquid-crystal display 20 and simultaneously supplies a corresponding value of the time base signal on output lines 46 as a column address signal. The algorithm just described facilitates real-time display of an ECG signal on presently available dot-matrix, liquid-crystal displays, which are not fast enough to display all the samples of an ECG signal that are required for an accurate and useful tracing. For example, it is very important for proper diagnosis to know the amplitude and timing of the R-wave, yet sampling of the ECG signal at speeds within the response capability of conventional LCDs, i.e., one sample every 50–150 msec. is likely to miss the peak of the R-wave.

Liquid-crystal display 20 responds to the row and column address signals supplied by microprocessor 28 by creating a tracing representative of the ECG signal obtained from the paddle electrodes. Microprocessor 28 generates time base signals for ECG display in real time at alternative rates of 1, 2.5, 5 or 10 cm per second on the liquid-crystal display in the manner of a strip-chart recorder. A suitable switch (not shown) is provided to select the desired display rate. Microprocessor 28 is also provided with a signal processing algorithm for further filtering out noise on the ECG signal associated with the dry electrodes.

Monitor 10 also has an automatic "on" feature whereby microprocessor 28 normally operates in a low-power quiescent or "sleep" mode and is activated in response to detection of skin contact by microprocessor 28. The microprocessor periodically reads data from A/D converter 26 (step 100 of FIG. 3) and becomes active for signal processing and display only if the data sample being read is within a predetermined range, as determined in decision block 102. If the sample is not within range, the microprocessor determines in step 104 whether it is in a "freeze frame" time period, which will be described below. Assuming the answer is no, the microprocessor executes the necessary steps in block 106 to remain in or return to "sleep" mode. Block 106 also represents the program steps which provided for periodic reading of data in step 100, i.e., a wait loop. If the sample checked in decision block 102 is within range, skin contact is considered to be made, whereupon the microprocessor "wakes up." The steps necessary to "wake up" the microprocessor are represented by block 108, which also represents the steps performed to check whether the microprocessor is already active. This feature prolongs the battery life. Alternatively, the automatic "on" feature may be implemented by means of switches mounted on the housing between the electrodes or interposed between the electrodes and the housing such that the mechanical action of pressing the monitor against the patient's chest closes a circuit which connects the battery to the monitor circuitry.

Another advantageous feature is "freeze frame" display after removal of the monitor 10 from the patient's skin. The data for maintaining the display in the state existing prior to removal of the electrodes is stored in RAM 36 and is continually supplied to LCD 20 for a preset period, after which the display is turned off. The "freeze frame" loop is illustrated in FIG. 3 as decision block 104 and output block 118. Program steps in decision block 104 cause "freeze frame" display to be initiated once monitor 10 is determined to have been removed from the patient's skin and to continue for a preset period thereafter. Step 118 is repeatedly executed during that period. Before removal of monitor 10 is detected, as well as after the preset period, the answer to the question in decision block 104 is no, and program control proceeds to step 106. All the ECG data in RAM 36 are available for later recall and transfer to a conventional chart recorder or other device.

Several different types of microprocessors are suitable for use in an ECG monitor according to the invention. For maximum miniaturization, the complete circuit for the monitor as described above is incorporated in a single hybrid circuit. Thus, in addition to satisfying the specifications described above, the microprocessor is preferably capable of integration in a hybrid circuit. The following microprocessors and microprocessor families, all 8-bit devices, are suitable for these purposes: Rockwell 6502; Zilog Z80C; RCA 1804 or others in the 1800 family; Motorola MC146805 or others in the 6800 family; and Hitachi 6305 or others in the 6300 family.

Liquid-crystal display 20 is an elongated, flat-screen, dot-matrix liquid-crystal display with a refresh rate of about 30 frames per second. Several currently available LCDs have sufficient speed for real-time ECG display using the techniques disclosed herein. Examples of these are Epson Model No. EG-Y84320AT and Seiko Model No. 4816. The Epson device has 32 rows and 84 columns, and the Seiko device has 64 rows and 480 columns. It will thus be appreciated that only 6 bits are required to obtain row addresses for 64 rows, and 5 bits for 32 rows. Consequently, only the most significant 5 bits (Epson) or 6 bits (Seiko) generated by A/D converter 26 are displayed. Although not required for display of a tracing on the LCDs just described, all 8 bits for each ECG signal sample are retained in memory for output to a chart recorder or other device.

The portable ECG monitor of the present invention allows more rapid diagnosis of life-threatening cardiac arrthymias in emergency situations by medical technicians, nurses, and physicians. It will be recognized that a simple pocket monitor that provides crucial information during the first few minutes after a heart attack while conventional equipment is being sought, assembled and prepared for use, has clear clinical potential.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. A pocket-sized, self-contained electrocardiogram monitor, comprising:
   (a) a pocket-sized housing having first and second sides;
   (b) a plurality of electrodes mounted on said second side of said housing;
   (c) circuit means contained within said housing for processing an electrocardiogram signal appearing upon said electrodes when said electrodes are placed in contact with a patient's chest, said circuit means including
      (1) means for selectively amplifying small signals near the baseline of said electrocardiogram signal without clipping said electrocardiogram signal;
      (2) A/D converter means for converting said electrocardiogram signal to a digital signal; and
      (3) digital processing means coupled to said A/D converter means for sampling said digital signal, selecting the maximum and minimum values in a set of at least four consecutive samples, and generating display drive signal values representative of said maximum and minimum values at a rate which is an integral fraction of the sampling rate; and
   (d) a dot-matrix, liquid-crystal display on said first side of said housing, said liquid-crystal display being coupled to said circuit means and responsive thereto to display said display drive signal values.

2. The electrocardiogram monitor of claim 1, further comprising:
   (e) means for activating said circuit means when said electrodes contact the skin of a patient.

3. The electrocardiogram monitor of claim 2, further comprising:
   (f) means for maintaining a display of a processed electrocardiogram signal for a preset period of time after said electrodes are removed from the skin of a patient.

4. The electrocardiogram monitor of claim 3 wherein said electrodes are dry electrodes mounted in line.

5. A pocket-sized, self-contained electrocardiogram monitor, comprising:
   (a) a pocket-sized, elongated housing having front and back sides parallel to its longitudinal axis;
   (b) three dry electrodes mounted on said back side of said housing in a line parallel to said longitudinal axis;
   (c) circuit means contained within said housing and coupled to said electrodes for converting an analog electrocardiogram signal appearing upon said electrodes to a digital electrocardiogram signal, for selecting the maximum and minimum values in every four consecutive samples of said digital electrocardiogram signal, and for generating a display drive signal representative of said maximum and minimum values at a rate which is an integral fraction of the sampling rate, said circuit means including means for generating a digital time base signal;

(d) an elongated, dot-matrix, liquid-crystal display mounted on said front side of said housing with its rows of display elements situated parallel to said longitudinal axis of said housing, said liquid-crystal display having row and column inputs connected to said circuit means so as to receive, respectively, said display drive signal and said digital time base signal;

(e) storage means for storing a larger portion of the digital electrocardiogram signal than the portion displayed on said display;

(f) means for recalling a stored portion of the digital electrocardiogram signal from said storage means and for supplying the recalled portion to said row input of said display; and (g) means included within said circuit means for selectively amplifying small signals near the baseline of an electrocardiogram signal without clipping the electrocardiogram signal.

6. The electrocardiogram monitor of claim 5, further comprising:

(h) means for activating said circuit means when said electrodes contact the skin of a patient.

7. The electrocardiogram monitor of claim 6, further comprising:

(i) means for maintaining a display of an electrocardiogram signal for a preset period of time after said electrodes are removed from the skin of a patient.

* * * * *